(12) United States Patent
Gaspari

(10) Patent No.: US 6,672,308 B1
(45) Date of Patent: Jan. 6, 2004

(54) ENDOTRACHEAL INTUBATION CONTROL ASSEMBLY

(75) Inventor: Romolo J. Gaspari, Stony Brook, NY (US)

(73) Assignee: JNC Medical, LLC, Stonybrook, NY (US)

(*) Notice: Subject to any disclaimer, the term of this patent is extended or adjusted under 35 U.S.C. 154(b) by 0 days.

(21) Appl. No.: 09/415,113

(22) Filed: Oct. 8, 1999

(51) Int. Cl.[7] .............................................. A61M 16/00
(52) U.S. Cl. ............................ 128/207.14; 128/200.26; 128/899
(58) Field of Search ................................. 128/899, 877, 128/869, 870, DIG. 26, DIG. 23, 207.17, 207.14, 207.15, 200.26; 600/424, 433, 434, 12, 15; 602/18

(56) References Cited

U.S. PATENT DOCUMENTS

| 3,996,939 A | * 12/1976 | Sheridan et al. ....... 128/207.14 |
| 4,063,561 A | 12/1977 | McKenna ................... 128/351 |
| 4,244,362 A | 1/1981 | Anderson ............... 128/200.26 |
| 4,576,150 A | 3/1986 | Auracher ..................... 128/75 |
| 4,955,368 A | 9/1990 | Heimann ..................... 128/75 |
| 5,257,636 A | * 11/1993 | White .................... 128/200.26 |
| 5,287,848 A | 2/1994 | Cubb et al. ............ 128/200.26 |
| 5,353,807 A | 10/1994 | DeMarco .................... 128/772 |
| 5,431,640 A | 7/1995 | Gabriel ........................ 604/270 |
| 5,560,351 A | 10/1996 | Gravenstein et al. .. 128/200.26 |
| 5,606,980 A | 3/1997 | Calhoun et al. ............. 128/772 |
| 5,788,658 A | 8/1998 | Islava ........................... 602/18 |
| 5,797,713 A | 8/1998 | Tweardy et al. ............ 411/339 |
| 5,819,734 A | * 10/1998 | Deily et al. ............ 128/207.15 |
| 5,843,153 A | 12/1998 | Johnston et al. |

* cited by examiner

*Primary Examiner*—Weilun Lo
*Assistant Examiner*—Mital Patel
(74) *Attorney, Agent, or Firm*—David M. McConoughey

(57) ABSTRACT

A control assembly for guiding the placement of an endotracheal tube during the intubation of a patient comprising a flexible stylet comprising a first magnet distally disposed on the stylet and an alignment fixture comprising a second magnet and adapted for positioning the second magnet over the cricothyroid cartilage of the patient to be intubated and retaining the second magnet in position over the cricothyroid cartilage of the patient.

49 Claims, 6 Drawing Sheets

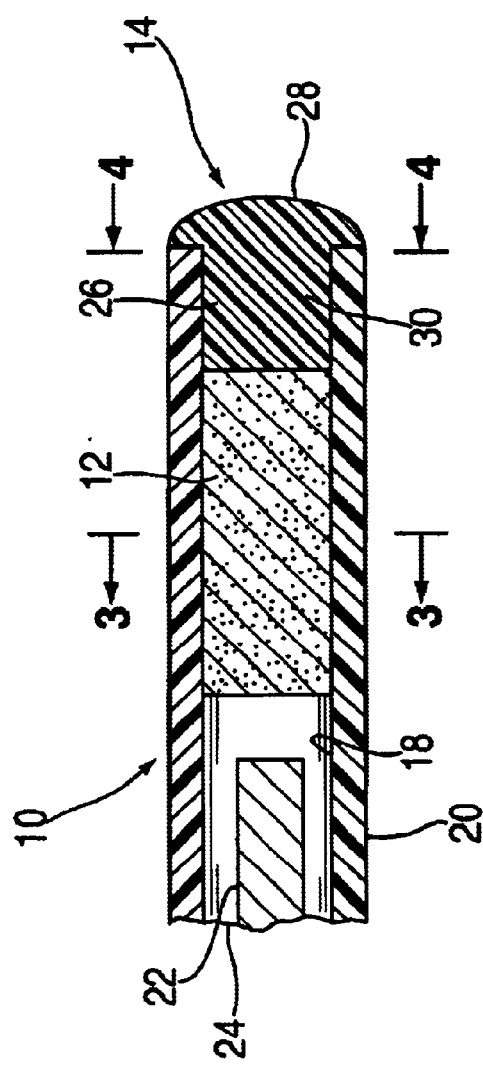
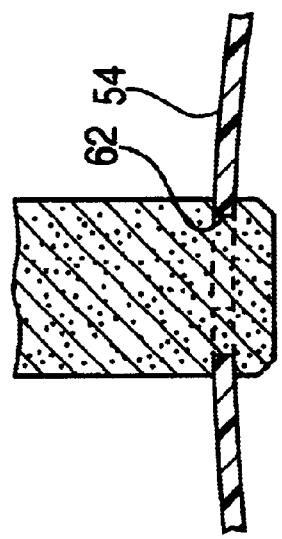
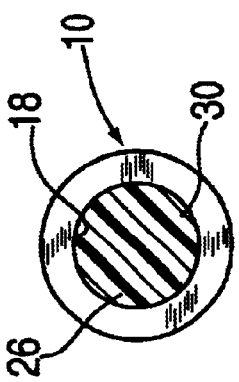
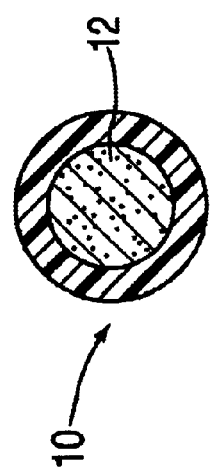

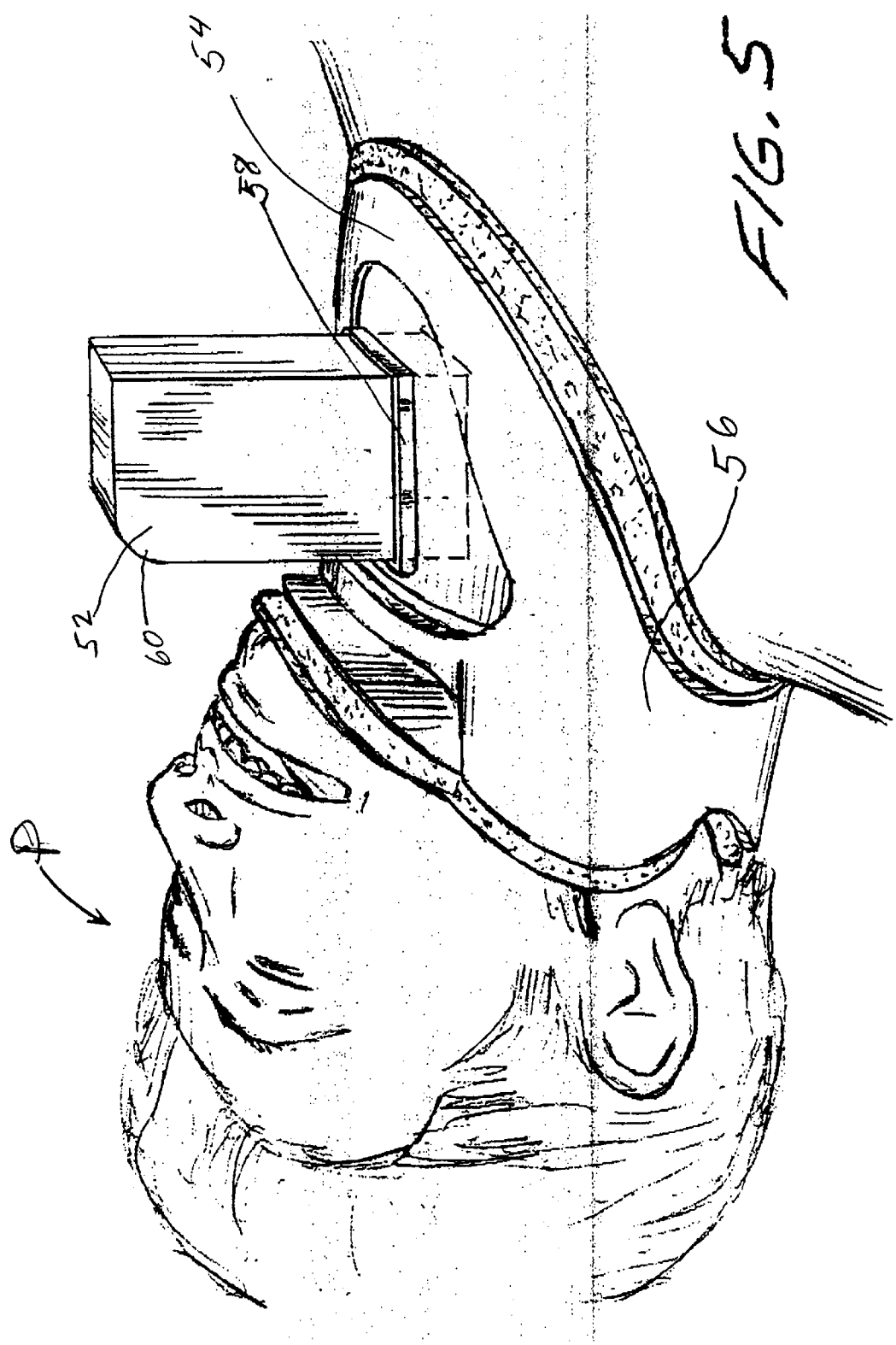

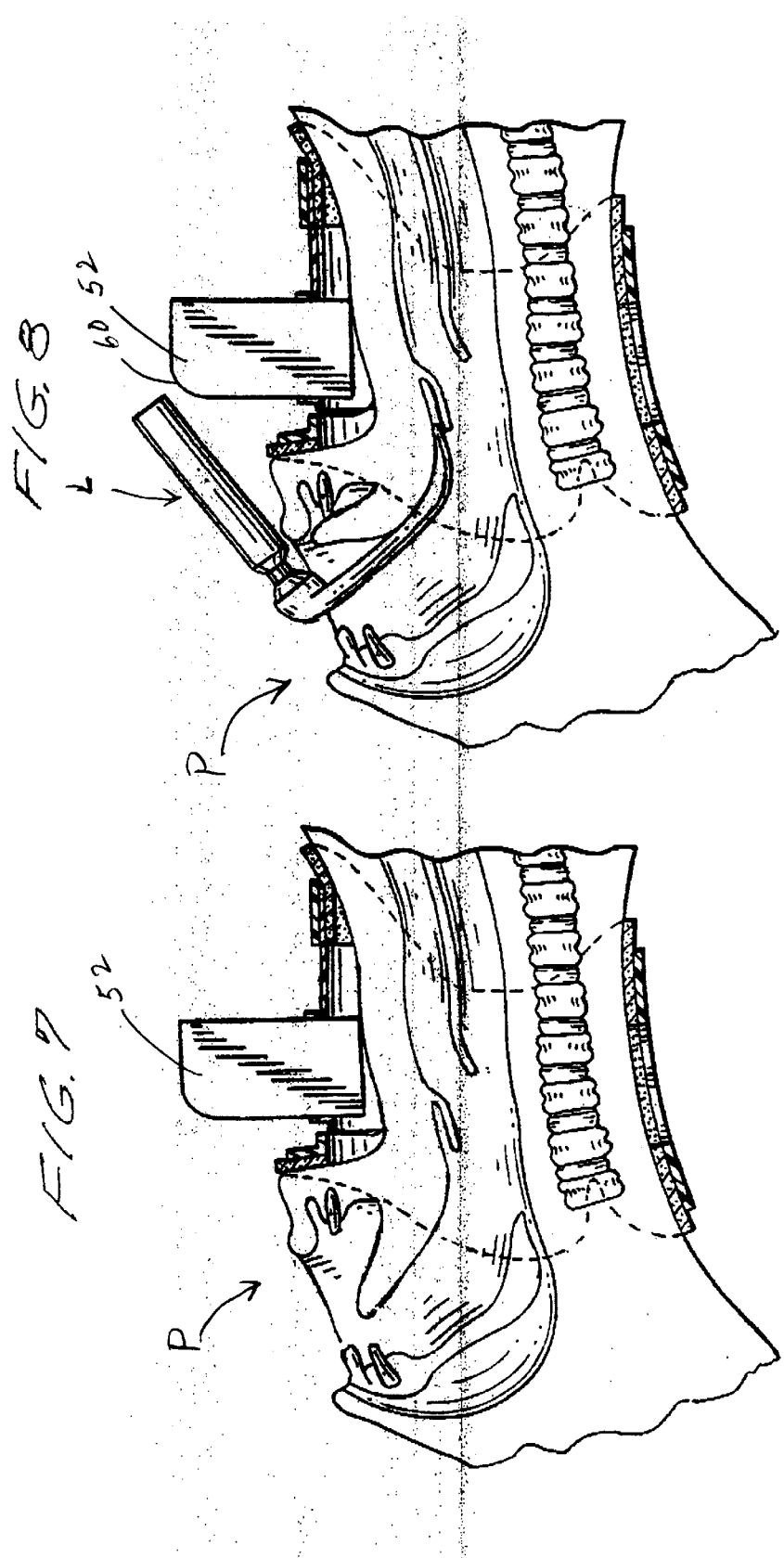

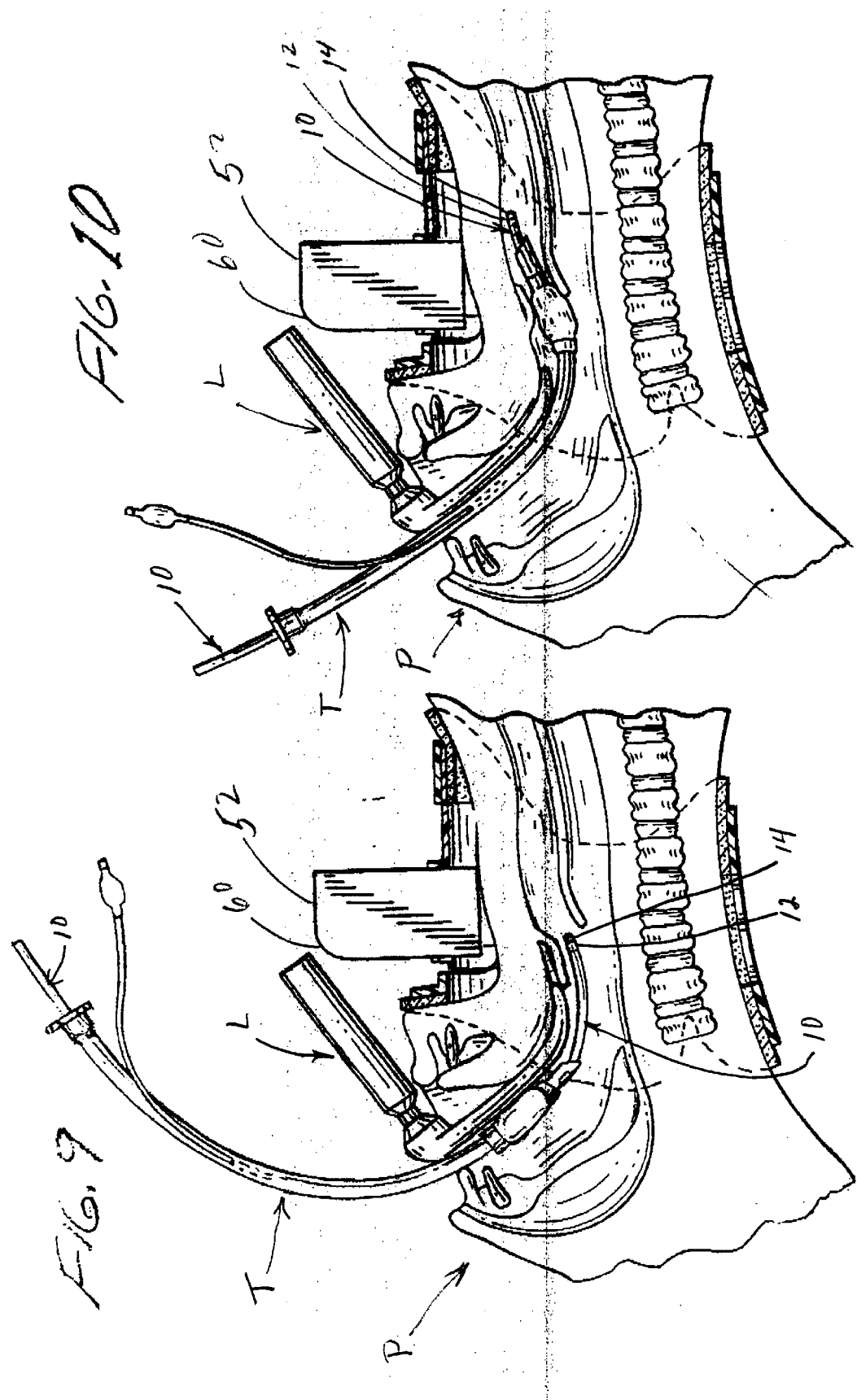

ENDOTRACHEAL INTUBATION CONTROL ASSEMBLY

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates generally to devices for the endotracheal intubation of a patient. More particularly, it relates to a control assembly for guiding the placement of an endotracheal tube during the intubation of a patient.

2. Description of the Related Art

In a medical context, it is important to maintain a patent airway in a patient so that the patient's respiration can be maintained either through the patient's own efforts or through external assistance. Even if the patient presents for medical care with a patent airway, it may be necessary to ensure that the airway remains patent, such as in assisted respiration by positive ventilation. Under these and other like circumstances it may become necessary to insert a tube from the exterior of the patient into the trachea so that respiratory or other gases can be ventilated directly to the lungs. This is accomplished by inserting an endotracheal tube through the mouth and ultimately into the trachea with the distal end of the tube disposed beyond the vocal chords. It is important that the endotracheal tube enter the trachea and not the esophagus so that any positive pressure is applied to the trachea and lungs and not the esophagus and gastrointestinal tract. Previously, in order to ensure this positioning, medical personnel performing this intubation visualized the vocal chords as the endotracheal tube was passing between the vocal chords and into the trachea beyond the vocal chords, thereby avoiding entry into the esophagus.

In the course of intubating a patient, the patient is typically placed in a prone position and the patient's head is extended and the lower jaw raised. From a position behind the patient's head the physician attempts to visualize the patient's vocal chords and then proceed with the intubation. Under certain circumstances, such as traumatic injury to the cervical spine or suspected injury to the cervical spine, movement of the patient or the patient's head, neck or lower jaw is contraindicated. In other circumstances the neck may not be able to be manipulated at all, such as rheumatoid arthritis or ankalosing spondylitis. In addition, patients presenting with preexisting abnormalities, such as, but not limited to, anatomical abnormalities of the neck or jaw;
  abnormally large tongue
  anatomical abnormalities of the lips or palate;
  arthritic cervical spine or tempomandibular joint;
  inelastic scar tissue of the face, neck or mouth;
  burns of the face, mouth, or throat;
  tumors or inflammation of the pharynx, larynx, trachea, esophagus, tonsils, uvala,
    retropharyngal space, or vocal chords;
  crush injuries to the larynx;
  jaw fractures;
  facial fractures;
  thyroid disease;
  spatial deviation of the epiglottis, vocal cords or trachea from the midline of the body;
  micrognathia;
  foreign body in the airway;
  caustic injections; and
  allergic reactions.

To further add to the difficulty of successful intubation, in traumatic intubation the foregoing problems may be overshadowed by additional concerns of a trauma patient, such as unstable cervical spine, flail chest, tension pneumothorax. These additional concerns decrease the amount of time available to secure the patency of the airway. Further, rather than wait until the patient is hospitalized, it would be desirable to provide a patent airway as rapidly and as reliably as possible. And it would also be highly desirable to provide a means for nonspecialist physicians and other nonphysician medical personnel, including physician extender personnel, such as physician assistants and respiratory therapists, to intubate reliably, rapidly and competently.

Previously, the options available for securing a patent airway in the emergency room or before hospital admittance were essentially either nasotracheal or orotracheal intubation requiring a high level of physician skill at the specialist level and the visualization of the vocal chords or a surgical procedure, such as cricthyrotomy, tracheotomy or transtracheal jet ventilation.

Techniques that utilized magnetic means for guiding a stylet into the trachea required skill in properly placing an external magnet with respect to the patient's anatomical landmarks vis a vis the esophageal/tracheal juncture and required continued manual stabilization of the external magnet and retention of that required placement during the intubation procedure. As a consequence two people were needed to perform these techniques. This was particularly undesirable in emergency, trauma and other critical medical emergencies where requiring the physician to use one hand to retain the placement of the external magnet severely reduced the ability of a single physician to intubate the patient.

BRIEF SUMMARY OF THE INVENTION

It is therefore an object of the present invention to desirably provide a means for performing endotracheal intubation without requiring manual retention of the intubation guide means in a fixed alignment position.

It is a further object to desirably provide a means for trauma specialist; emergency medicine physicians and anesthesiologists to perform endotracheal intubation more rapidly and more reliably in a variety of difficult situations.

It is a still further object to desirably provide a means for non specialist physicians and even physician extender personnel, such as physician assistants and respiratory therapists to perform endotracheal intubation.

These and other objects may be desirably provided by a control assembly for guiding the placement of an endotracheal tube during the intubation of a patient configured in accordance with the present invention that comprises a. A flexible stylet comprising a first magnetic means distally disposed on said stylet and
  b. An alignment fixture comprising a second magnetic means and adapted for positioning the second magnetic means over the cricothyroid cartilage of the patient to be intubated and retaining the second magnetic means in position over the cricothyroid cartilage of the patient.

BRIEF DESCRIPTION OF THE SEVERAL VIEWS OF THE DRAWINGS

FIG. 2 is an illustration in side section of the distal end of the stylet of the alignment fixture of the present invention;

FIG. 3 is an illustration in lateral cross-section of the distal end of the stylet of the alignment fixture of the present invention taken along the line 3—3 of FIG. 2;

FIG. 4 is an illustration in lateral cross-section of the distal end of the stylet of the alignment fixture of the present invention taken along the line 3—3 of FIG. 2;

FIG. 5 is an illustration of the alignment fixture of the present invention emplaced on a patient in the supine position;

FIG. 7 is an illustration in side section of the anatomy of a patient prior to commencement of an endotracheal intubation using the control assembly of the present invention;

FIG. 8 is an illustration in side section of the anatomy of a patient showing the insertion of a standard MacIntosh laryngoscopic blade during an endotracheal intubation using the control assembly of the present invention;

FIG. 9 is an illustration in side section of the anatomy of a patient showing insertion of an endotracheal tube and a stylet of the present invention during an endotracheal intubation using the control assembly of the present invention;

FIG. 10 is an illustration in side section of the anatomy of a patient showing the attraction of the first and second magnets of the present invention during an endotracheal intubation using the control assembly of the present invention; and FIG. 11 is an illustration in side section of an alternative embodiment of the means of affixing the external magnet to the alignment fixture of the present invention

DETAILED DESCRIPTION OF THE INVENTION

Figure 1:
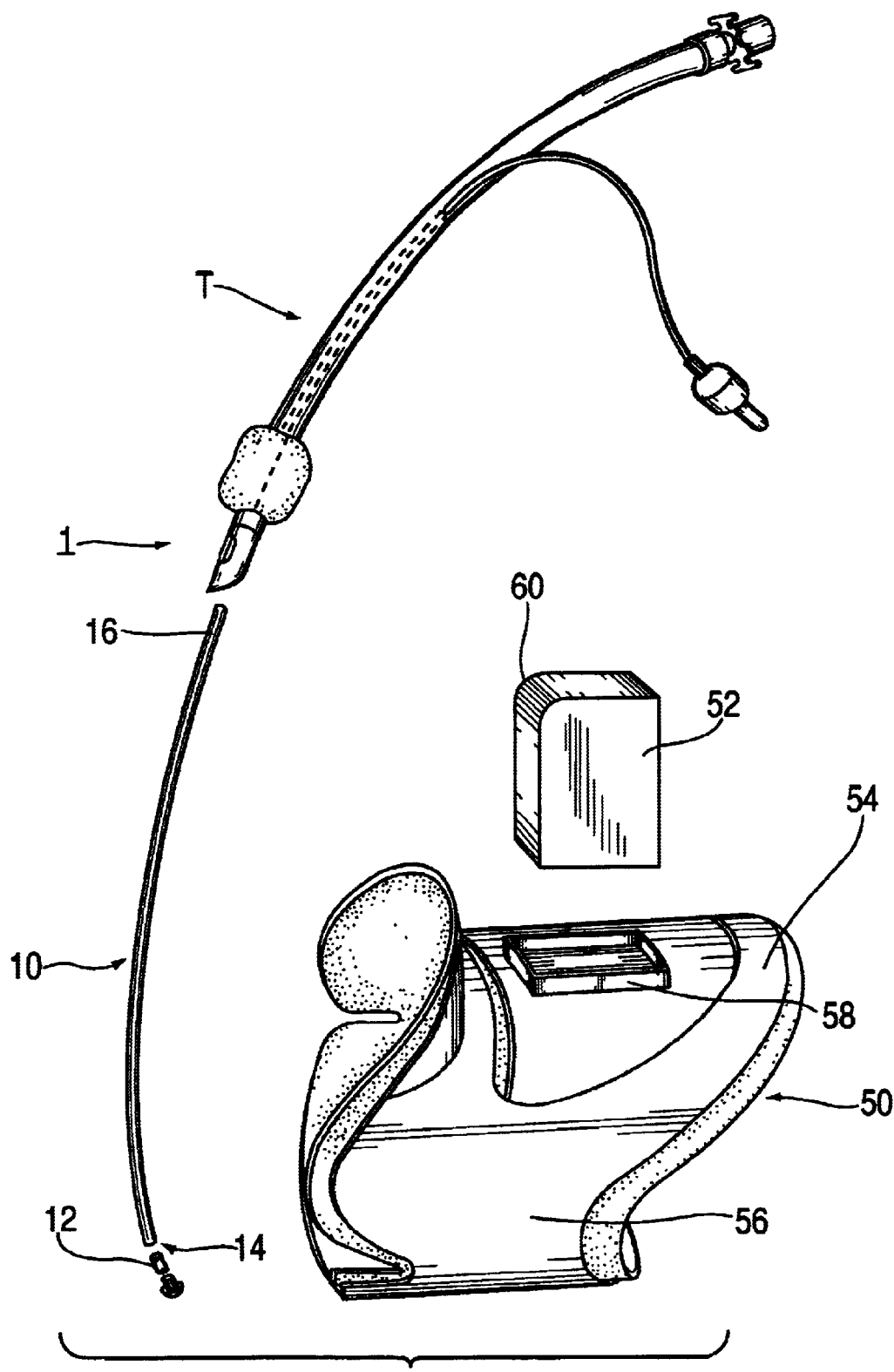
FIG. 1 is an illustration of the components of the control assembly of the present invention.

With reference to the drawings, and particularly FIG. 1, a control assembly 1 of the present invention for guiding the placement of an endotracheal tube during the orotracheal intubation of a patient comprises a flexible stylet 10 with a first magnetic means 12, such as a magnet, distally disposed on it and an alignment fixture 50 comprising a second magnetic means 52, such as a permanent magnet, that is adapted for positioning the second magnetic means 52 over the cricothyroid cartilage of a patient P to be intubated.

Figure 6:
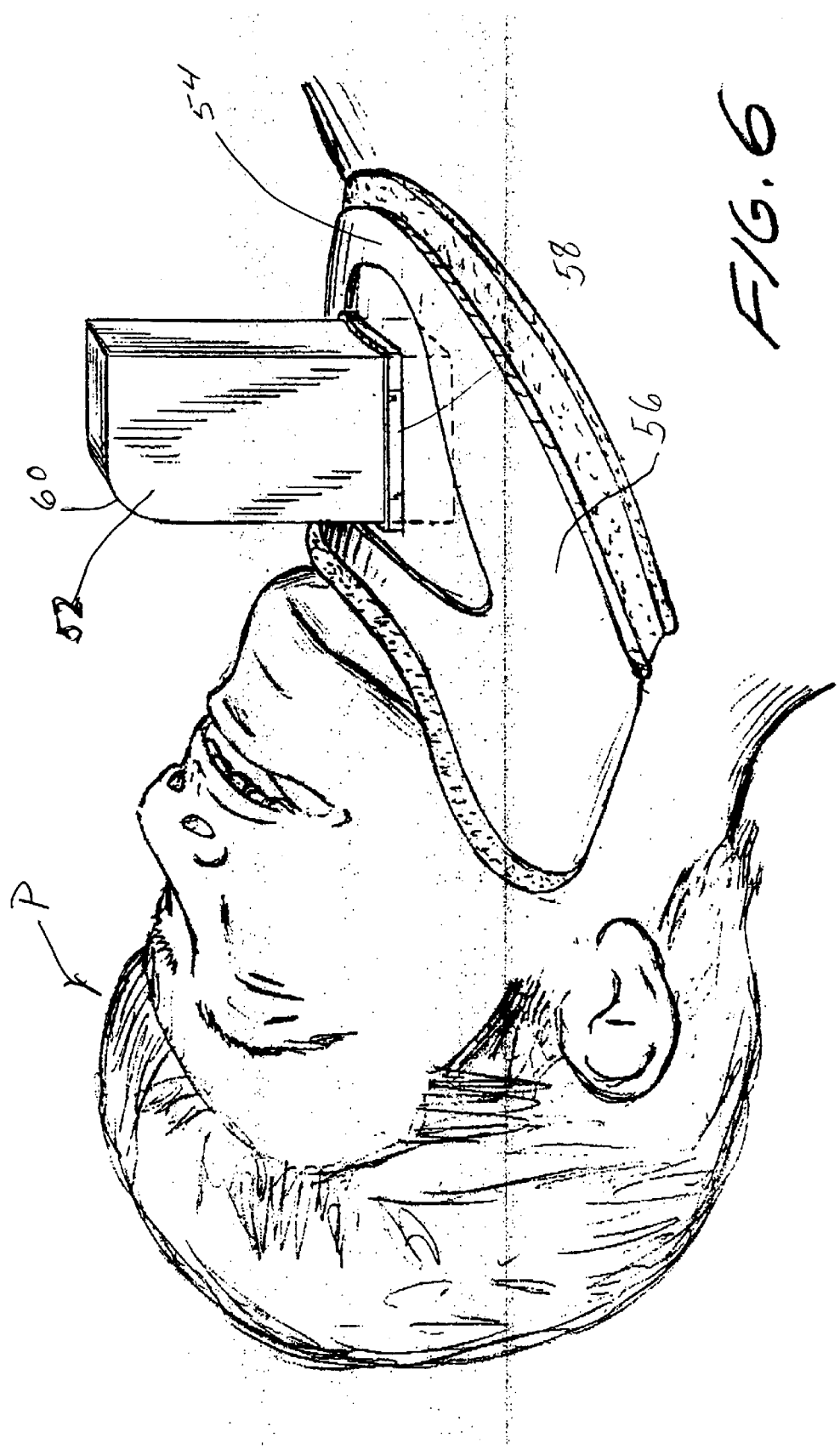
FIG. 6 is an illustration of an alternative embodiment of the alignment fixture of the present invention emplaced on a patient.

The alignment fixture 50 (FIGS. 1, 5 and 6) is desirably configured to
  a. automatically position the second magnet 52 in alignment with the anterior surface of the cricothyroid cartilage so that the longitudinal central axis of the magnetic field of the second magnet 52 passes posterior to the anterior reflection of the cricothyroid cartilage; and
  b. retain the second magnet 52 in alignment without requiring that the alignment fixture 50 be manually held in position.

In transverse cross section the alignment fixture 50 is generally semicylindrical, such that it comprises a central apron 54 and a pair of opposed, arcuate side aprons 56 that extend circumferentially and laterally at least partially around the patient's neck. The second magnet 52 is affixed to the fixture 50 by a surrounding edge engaging the magnet on at least two sides (FIG. 11) or, alternatively, an upstanding flange 58 enclosing the lower end of the second magnet 52 and and supporting the second magnet 52 against movement with respect to the central apron 54. The flange 58 may be affixed to the apron 54 by fasteners or by other means, such as adhesive. As shown (FIGS. 1, 5 and 6) it may prefderably be formed integrally with the apron 54. The apron 54 may, optionally be provided with an aperture to permit visualization of the cricothyroid cartilage as the alignment fixture 50 is initially emplaced of the patient's neck. The upper, superior edge 60 of the external magnet 52 is rounded to limit interfering interaction with the handle of the laryngoscope. While the external magnet 52 has been shown as a rectangular prism solid with a curved upper, superior edge, the external magnet 52 may be generally cylindrical with a rounded upper edge, or even hemispherical end, to provide clearance for a laryngoscopic device. The external magnet 52 is preferably removable from the apron. As may be seen in FIG. 11, it may be provided with a groove 62 so as to be slidable into the aperture and lock into place with the edges of the apron 54 of the alignment fixture 50 registered, and engaged by, the groove 62 to allow a firm, but removable, placement.

When the alignment fixture 50 has been emplaced on the patient's neck with the second magnet 52 aligned with respect to the cricothyroid cartilage, it will remain in place, thereby freeing the physician or other medical personnel to use both hands for other duties.

In an alternative embodiment (FIG. 5), the side aprons 56 extend circumferentially to form an enclosed arc so that the fixture 50 completely encircles the patient's neck, thereby further stabilizing the fixture against movement of the second magnet 52 out of alignment. In this embodiment the alignment fixture 50 may take the form of a cervical collar, thereby integrating the alignment features of the present invention with the cervical fixation of the enclosing collar. In this embodiment, the cervical fixation also serves to fix the alignment of the second magnet 52 by immobilizing the neck against movement of the cricothyroid cartilage with respect to the second magnet 52. In addition, the collar is self-aligning since the upper edge of the collar presses against the angle of the lower jaw and the occiput and the lower edge presses against the clavicles, sternum, shoulders and chest wall.

The flexible stylet 10 (FIGS. 1–4) is desirably comprised of a length of polymeric tubing with a terminal first magnetic means 12, or permanent magnet disposed at its distal tip 14. Optionally, the proximal end 16 may be provided with a textured surface, handle or other gripping surface for the operator to grip in order to advance and retract the stylet 10 during the intubation procedure. The stylet 10 is flexible to allow flexure with respect to its longitudinal central axis and yet sufficiently stiff that it can be advanced and retracted along the patient's oropharyngial tract. Its length should be about one and one-half times the length of the endotracheal tube it is emplacing. The diameter may be from about one millimeter to about eight millimeters and preferably from about four millimeters to about seven millimeters. A 6 French stylet may be used in association with a 2.0 millimeter to 3.5 internal diameter millimeter endotracheal tube; a 10 French stylet with a 4.0 millimeter to 6.5 millimeter internal diameter endotracheal tube; a 12 French stylet with a 5.0 millimeter to 10.0 millimeter internal diameter endotracheal tube; and a 14 French stylet with a 7.0 millimeter to 10.0 millimeter internal diameter endotracheal tube;

The stylet 10 is annular in transverse cross section with an inner wall 18 and an outer wall 20. The outer wall 20 may be particularly adapted to facilitate advancement and retraction along the patient's oropharyngial tract. The distal tip 14 of the stylet 10 may be curved or rounded to prevent injury and to guide the stylet around obstructions. The internal magnet 12 is fitted into the central bore 24 at the distal tip 14 and the end of the stylet 10 is preferably terminated with a plug 26 with an enlarged diameter head 28 and a reduced diameter base 30. The transverse diameter of the head 28 is generally equal to the diameter of the outer wall 20 to provide a smooth profile. The diameter of the base 30 is generally the same as the diameter of the inner wall 18 to provide a snug fit. Similarly, the maximum transverse diameter of the internal magnet 12 should be generally the same as the diameter of the inner wall 18 to produce a snug fit so that the magnet 12 does not shift in position.

The flexibility of the stylet 10 may be changed and its rigidity altered by inserting a stiffening member 22, such as a wire, into the central bore 24 of the stylet tubing. The wire 22 may be bent into a shallow arcuate curve to generally conform to the general curvature of the patient's orolaryngial tract as defined by the upper central incisors, the rear of the soft palate and the posterior wall of the laryngopharynx. The wire 22 is designed to retain any conformation it is formed into prior to the intubation. The stiffening member 22 may comprise a wire composed of aluminum, stainless steel or copper. The stiffening member 22 may also be a rod of polymeric material. The stiffening member 22 may be from about 0.2 millimeter to about 2 millimeters in diameter, preferably about one millimeter.

The first and second magnets 12 and 52, respectively, are of opposite polarity to each other and may be comprised of a rare earth-based magnetic material, such as neodymium. In addition, one of the magnets, such as, preferably, the internal magnet 12 disposed on the stylet, may be substituted with a material that, while not a magnet, is attractive to a magnet. Consequently, the terms "magnet" and "magnetic means" should be construed, as appropriate, to include a material that is attractive to a magnet, with the proviso that the other magnet or magnetic means is a magnet.

A laryngoscopic device L, such as a laryngoscopic blade, is inserted into the patient's oropharynx for anteriorly displacing the soft tissue of the anterior pharynx of the patient.

In using the control assembly 1 of the present invention, the patient P is placed in a supine position (see FIG. 7) a laryngoscopic blade L is inserted into the mouth and the distal tip is passed through the oropharynx and into the vallecula, or over the epiglottis, so that the soft tissue of the patient's anterior pharynx, including the epiglottis, are displaced anteriorly by the anterior surface of the laryngoscopic blade L. (See FIG. 8) The flexible stylet 10, having been inserted into the lumen of the endotracheal tube T with the distal tip 14 of the flexible stylet 10 extending beyond the distal end of the endotracheal tube with the first magnet 12 and a length of the flexible stylet 10 , such as about one to three centimeters, being free of the endotracheal tube so that the stylet 10 can freely flex, is introduced into the patient's mouth inferiorly of the laryngoscopic blade. The flexible stylet 10 may be advanced independently of the endotracheal tube or the two may be advanced as a unit, preferably with the first magnet 12 and a length of stylet 10 being free to flex, such as about one to three centimeters of the stylet 10. The stylet 10 (or stylet/endotracheal tube combination, as the case may be) is inserted into the oropharynx passed the vallecula and then the epiglottis. (See FIG. 9.) The advancement of the stylet 10 (or the stylet/endotracheal tube combination) is temporarily halted when the magnet is in the posterior oropharynx to allow magnetic attraction between the first magnet 12 and the second magnet 52. Then, the alignment fixture 50 is placed on the patient's throat. (See FIG. 10.) Owing to the fixture's construction, the second magnet 52 is aligned with the patient's cricothyroid cartilage—an anatomical landmark associated with, and next to, the juncture of the trachea and the esophagus. The physician's hands are both free to complete the intubation or for other tasks. Then, the stylet 10 (with or without the endotracheal tube T) is advanced passed the vallecula and epiglottis. As the stylet 10 (or stylet/endotracheal tube combination) is further extended, the stylet 10 flexes anteriorly with the distal tip 14 being deflected toward the opening of the trachea owing to the magnetic attraction between the first magnet 12 on the flexible stylet 10 and the second magnet 52 on the alignment fixture 50. As the stylet 10 (or stylet/endotracheal tube combination) is advanced further, this attraction guides the distal tip 14 of the stylet 10 through the vocal chords and beyond them. No visualization of the vocal cords is needed to complete the placement of the endotracheal tube T. Once the distal tip 14 of the stylet 10 has reached this point beyond the vocal cords, the endotracheal tube T is extended along the stylet 10 until the distal end 14 of the endotracheal tube T has passed through the vocal chords and reached the trachea adjacent the cricothyroid cartilage, the stylet 10 acting as a guide for this insertion. Once the distal end of the endotracheal tube is in place, the flexible stylet 10 is retracted into lumen of the endotracheal tube and then removed from the patient by withdrawal through the lumen.

In the alternative, and preferably when the side aprons of the alignment fixture fully encircle the patient's neck, the alignment fixture is emplaced before the foregoing procedure is commenced.

While the foregoing procedure has been described in terms of the use of a laryngoscopic device L, it is possible, in the alternative, to not use such device.

Additionally, nasotracheal intubation may be accomplished by introducing the stylet 10 (or the stylet/endotracheal tube combination) into the nasal opening and inferiorly into the posterior oropharynx. This is accomplished in an awake and breathing patient. The magnetic attraction of the two magnets is identical to the orotracheal approach from this point forward. This nasotracheal procedure may be utilized with the patient in a variety of positions from sitting to standing to lying down on the patient's side or back.

While the control assembly 1 of the present invention has been described and is particularly suitable for the endotracheal intubation of a human patient, it may also be adapted and used in the intubation of nonhuman subjects, such as in veterinary medical practice.

The preceding description and drawings are given for the purpose of illustration and not limitation. Material substitutions and variations are possible without departing from the invention.

Accordingly, the invention is to be limited only by the scope of the following claims.

I claim:

1. An endotracheal intubation assembly comprising
  a. an endotracheal tube and
  b. a control assembly for guiding the placement of an endotracheal tube during the intubation of a patient comprising i. a flexible stylet comprising a first magnet distally disposed on said stylet and
ii. an alignment fixture having a semicylindrical configuration and comprising a second magnet and adapted
1) for positioning the second magnet over the cricothyroid cartilage of the patient to be intubated and
2) for retaining the second magnet in position over the cricothyroid cartilage of the patient.

2. An endotracheal intubation assembly as defined in claim 2 wherein said alignment fixture comprises
   a. a central apron and
   b. a pair of opposed, arcuate side aprons.

3. An endotracheal intubation assembly as defined in claim 2 wherein said arcuate side aprons extend circumferentially to form an enclosed arc.

4. An endotracheal intubation assembly as defined in claim 1 wherein said second magnet is affixed to said alignment fixture by means of an upstanding flange.

5. An endotracheal intubation assembly as defined in claim 1 wherein said second magnet is removable from said alignment fixture.

6. An endotracheal intubation assembly as defined in claim 1 wherein said stylet comprises a distal end and said first magnet is disposed at the distal end of said stylet.

7. An endotracheal intubation assembly as defined in claim 1 wherein said stylet comprises a proximal end and the proximal end of said stylet is provided with a gripping surface.

8. An endotracheal intubation assembly as defined in claim 1 wherein said stylet is flexible.

9. An endotracheal intubation assembly as defined in claim 1 wherein said stylet is annular in transverse cross section.

10. An endotracheal intubation assembly as defined in claim 1 wherein said stylet is provided with a stiffening member.

11. An endotracheal intubation assembly as defined in claim 10 wherein said stiffening member is removable.

12. An endotracheal intubation assembly as defined in claim 11 wherein said stiffening member comprises a wire.

13. An endotracheal intubation assembly as defined in claim 11 wherein said stiffening member comprises a polymeric rod.

14. An endotracheal intubation assembly comprising
    a. an endotracheal tube and
    b. a control assembly for guiding the placement of an endotracheal tube during the intubation of a patient comprising
       i. a flexible stylet comprising a first magnet distally disposed on said stylet and
       ii. an alignment fixture having a semicylindrical configuration and comprising a second magnet and adapted
          1) for positioning the second magnet over the cricothyroid cartilage of the patient to be intubated and
          2) for retaining the second magnet in position over the cricothyroid cartilage of the patient,
wherein said second magnet is removable from said alignment fixture.

15. An endotracheal intubation assembly as defined in claim 14 wherein said alignment fixture comprises
    a. a central apron and
    b. a pair of opposed, arcuate side aprons.

16. An endotracheal intubation assembly as defined in claim 15 wherein said arcuate side aprons extend circumferentially to form an enclosed arc.

17. An endotracheal intubation assembly as defined in claim 14 wherein said second magnet is affixed to said fixture by means of an upstanding flange.

18. An endotracheal intubation assembly as defined in claim 14 wherein said second magnet is removable from said alignment fixture.

19. An endotracheal intubation assembly as defined in claim 14 wherein said stylet comprises a distal end and said first magnet is disposed at the distal end of said stylet.

20. An endotracheal intubation assembly as defined in claim 14 wherein said stylet comprises a proximal end and the proximal end of said stylet is provided with a gripping surface.

21. An endotracheal intubation assembly as defined in claim 14 wherein said stylet is flexible.

22. An endotracheal intubation assembly as defined in claim 14 wherein said stylet is annular in transverse,cross section.

23. An endotracheal intubation assembly as defined in claim 14 wherein said stylet is provided with a stiffening member.

24. An endotracheal intubation assembly as defined in claim 23 wherein said stiffening member is removable.

25. An endotracheal intubation assembly as defined in claim 24 wherein said stiffening member comprises a wire.

26. An endotracheal intubation assembly as defined in claim 24 wherein said stiffening member comprises a polymeric rod.

27. An endotracheal intubation assembly comprising
    a. an endotracheal tube and
    b. a control assembly for guiding the placement of an endotracheal tube during the intubation of a patient comprising
       i. a flexible stylet comprising a first magnetic means distally disposed on said stylet and
       ii. an alignment fixture comprising a second magnetic means and adapted
          1) for positioning the second magnetic means over the cricothyroid cartilage of the patient to be intubated and
          2) for retaining the second magnetic means in position over the cricothyroid cartilage of the patient.
wherein said alignment fixture comprises
    a. a central apron and
    b. a pair of opposed, arcuate side aprons.

28. An endotracheal intubation assembly as defined in claim 27 wherein said second magnet is affixed to said fixture by means of an upstanding flange.

29. An endotracheal intubation assembly as defined in claim 27 wherein said second magnet is removable from said alignment fixture.

30. An endotracheal intubation assembly as defined in claim 27 wherein said arcuate side aprons extend circumferentially to form an enclosed arc.

31. An endotracheal intubation assembly as defined in claim 27 wherein said stylet comprises a distal end and said first magnet is disposed at the distal end of said stylet.

32. An endotracheal intubation assembly as defined in claim 27 wherein said stylet comprises a proximal end and the proximal end of said stylet is provided with a gripping surface.

33. An endotracheal intubation assembly as defined in claim 27 wherein said stylet is flexible.

34. An endotracheal intubation assembly as defined in claim 27 wherein said stylet is annular in transverse cross section.

35. An endotracheal intubation assembly as defined in claim 27 wherein said stylet is provided with a stiffening member.

36. An endotracheal intubation assembly as defined in claim 35 wherein said stiffening member is removable.

37. An endotracheal intubation assembly as defined in claim 36 wherein said stiffening member comprises a wire.

38. An endotracheal intubation assembly as defined in claim 36 wherein said stiffening member comprises a polymeric rod.

39. An endotracheal intubation assembly comprising
   a. an endotracheal tube and
   b. a control assembly for guiding the placement of an endotracheal tube during the intubation of a patient comprising
      i. a flexible stylet comprising a first magnetic means distally disposed on said stylet and
      ii. an alignment fixture comprising a second magnetic means and adapted
         1) for positioning the second magnetic means over the cricothyroid cartilage of the patient to be intubated and
         2) for retaining the second magnetic means in position over the cricothyroid cartilage of the patient
   wherein said alignment fixture comprises
      a. a central apron and
      b. a pair of opposed, arcuate side aprons and
   wherein said arcuate side aprons extend circumferentially to form an enclosed arc.

40. An endotracheal intubation assembly as defined in claim 39 wherein said second magnet is affixed to said fixture by means of an upstanding flange.

41. An endotracheal intubation assembly as defined in claim 39 wherein said second magnet is removable from said alignment fixture.

42. An endotracheal intubation assembly as defined in claim 39 wherein said stylet comprises a distal end and said first magnet is disposed at the distal end of said stylet.

43. An endotracheal intubation assembly as defined in claim 39 wherein said stylet comprises a proximal end and the proximal end of said stylet is provided with a gripping surface.

44. An endotracheal intubation assembly as defined in claim 39 wherein said stylet is flexible.

45. An endotracheal intubation assembly as defined in claim 39 wherein said stylet is annular in transverse cross section.

46. An endotracheal intubation assembly as defined in claim 39 wherein said stylet is provided with a stiffening member.

47. An endotracheal intubation assembly as defined in claim 46 wherein said stiffening member is removable.

48. An endotracheal intubation assembly as defined in claim 46 wherein said stiffening member comprises a wire.

49. An endotracheal intubation assembly as defined in claim 46 wherein said stiffening member comprises a polymeric rod.

* * * * *